United States Patent [19]
Nakazeki et al.

[11] Patent Number: 5,798,454
[45] Date of Patent: Aug. 25, 1998

[54] MAGNETICALLY SUSPENDED DEVICE WITH FUNCTION OF MEASURING VISCOSITY

[75] Inventors: Tsugito Nakazeki, Shizuoka; Toshihiko Nojiri, Kanagawa, both of Japan

[73] Assignee: NTN Corporation, Osaka, Japan

[21] Appl. No.: 783,911

[22] Filed: Jan. 16, 1997

[30] Foreign Application Priority Data

Jan. 31, 1996 [JP] Japan .................................. 8-014859

[51] Int. Cl.⁶ .................................................. G01N 11/14
[52] U.S. Cl. ...................... 73/54.28; 73/54.35; 73/54.23
[58] Field of Search ........................ 73/54.01, 54.23, 73/54.28, 54.32, 54.35, 61–71; 417/63, 410.1, 420

[56] References Cited

U.S. PATENT DOCUMENTS

| | | | |
|---|---|---|---|
| 2,563,567 | 8/1951 | Wakefield | 73/54.32 |
| 4,781,525 | 11/1988 | Hubbard et al. | 45/30 |
| 5,350,283 | 9/1994 | Nakazeki et al. | 417/420 X |

*Primary Examiner*—Michael Brock
*Attorney, Agent, or Firm*—McDermott, Will, & Emery

[57] ABSTRACT

A rotor is magnetically suspended in liquid by a non-active magnetic bearing with opposed permanent magnets, a step shaped signal at constant voltage is generated from a signal generator, and supplied to an electromagnet of an active magnetic bearing, the response of the rotor at the time is detected by a position sensor, and viscosity equivalent to an damping coefficient is calculated by a CPU.

6 Claims, 4 Drawing Sheets

MAGNETICALLY SUSPENDED DEVICE WITH FUNCTION OF MEASURING VISCOSITY

BACKGROUND OF THE INVENTION

1. Field of the Invention

The present invention relates generally to magnetically suspended devices with the function of measuring viscosity, and more particularly, to such a magnetically suspended device with the function of measuring viscosity for use in medical equipment such as blood pump and an artificial heart-lung machine and capable of measuring the viscosity of blood.

2. Description of the Background Art

FIG. 6 is a diagram showing a conventional heart-lung machine. In FIG. 6, the artificial heart-lung machine is provided with a pressure meter 3 as measuring means in addition to a blood pump 1 and an artificial lung 2, and further requires a flow meter 4 if blood pump 1 is of centrifugal type. Upon using such an artificial heart-lung machine, blood is collected at fixed time intervals and examined for the state using another device. During the examination, use of a blood diluent changes the hematocrit or the blood viscosity, which also changes depending on the temperature of blood. Such change in the blood viscosity further changes the distribution of flow rates within the flow path. The change in the hematocrit or flow rate distribution causes errors in various flow meters as follows.

More specifically, an electromagnetic flow meter or a supersonic Doppler flow meter is used as a flow meter for an artificial heart-lung machine. In the electromagnetic flow meter, the conductivity of liquid greatly affects output voltage, the hematocrit affects the conductivity of blood, and therefore a change in the hematocrit causes errors in measurement. In the supersonic Doppler flow meter, a change in the flow rate distribution is a major cause for errors. The blood viscosity which changes the flow rate distribution affects the precision of measurement. If a flow meter is calibrated for each of hematocrit and viscosity, correction is possible using these values. Measurement of hematocrit or blood viscosity has required a batch processing involving blood collection, such correction cannot be achieved in real time.

SUMMARY OF THE INVENTION

It is therefore a main object of the present invention to provide a magnetically suspended device with the function of measuring viscosity which can measure blood viscosity in real time.

Briefly stated, a rotor is suspended in liquid by a magnetic bearing, the position of the suspended rotor is changed stepwise using a viscosity measuring device, and the viscosity of the liquid is calculated based on the response time of the rotor at the time.

According to the present invention, blood viscosity can be measured in real time.

In a preferred embodiment, a rotor is rotated in a non-contact manner by the driving force of an electric motor and functions as a pump.

More preferably, combination of a temperature and a viscosity provides blood information without collecting blood.

Further preferably, a warning signal is output if blood viscosity reaches a predetermined value or a value higher or lower than the value, which enables a quick treatment to a patient with an artificial heart-lung machine.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1C:
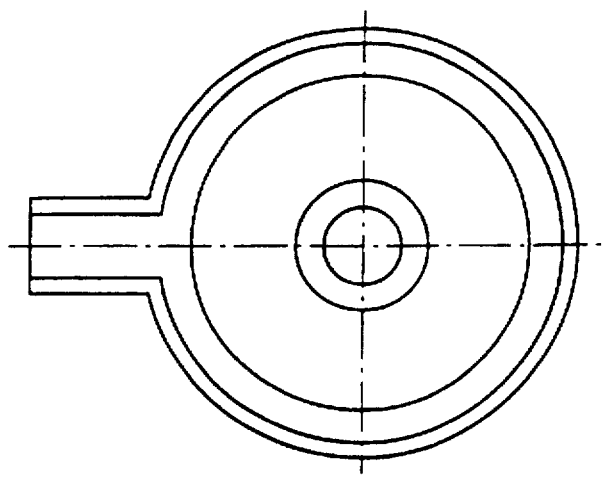
FIGS. 1A to 1C include views showing mechanical components of one embodiment according to the present invention.
Figure 1A:
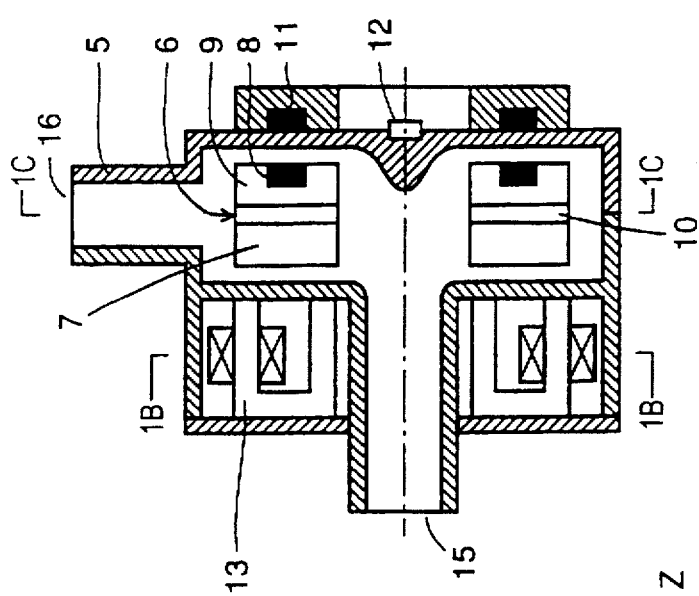
Figure 1B:
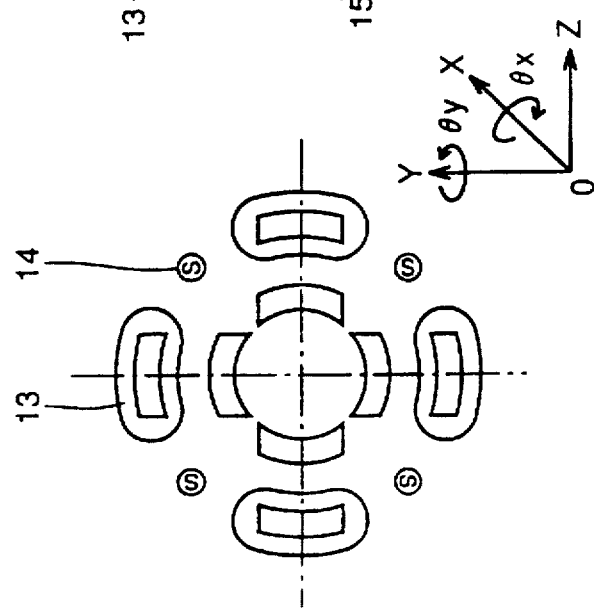

FIGS. 1A to 1C show mechanical components of one embodiment of the invention, wherein FIG. 1A is a side view in section, FIG. 1B is a cross sectional view taken along line 1B—1B at FIG. 1A and FIG. 1C is a cross sectional view taken along line 1C—1C at FIG. 1A.

In FIGS. 1A to 1C, a rotor 6 is formed of a magnetic body 7 made of stainless steel and a non-magnetic body 9 filled with a ring magnet 8. There is provided a flow path 10 between magnetic body 7 and non-magnetic body 9. On one side of casing 5, there is provided a permanent magnet 11 facing opposite to ring magnet 8. Ring magnet 8 and permanent magnet 11 are polarized along the axial direction, and function to attract each other. In the center of that one side of casing 5, there is provided a temperature sensor 12 for detecting the temperature of blood.

There is provided a magnetic bearing formed of an electromagnet 13 and a position sensor 14 on the other side of casing 5. Blood is input from an inlet 15 provided on the other side of casing 5, and output from an outlet 16. The active magnetic bearing in FIG. 1 is a 3-axes active magnetic bearing having Z, $\theta_x$ and $\theta_y$ controlled.

Figure 2:
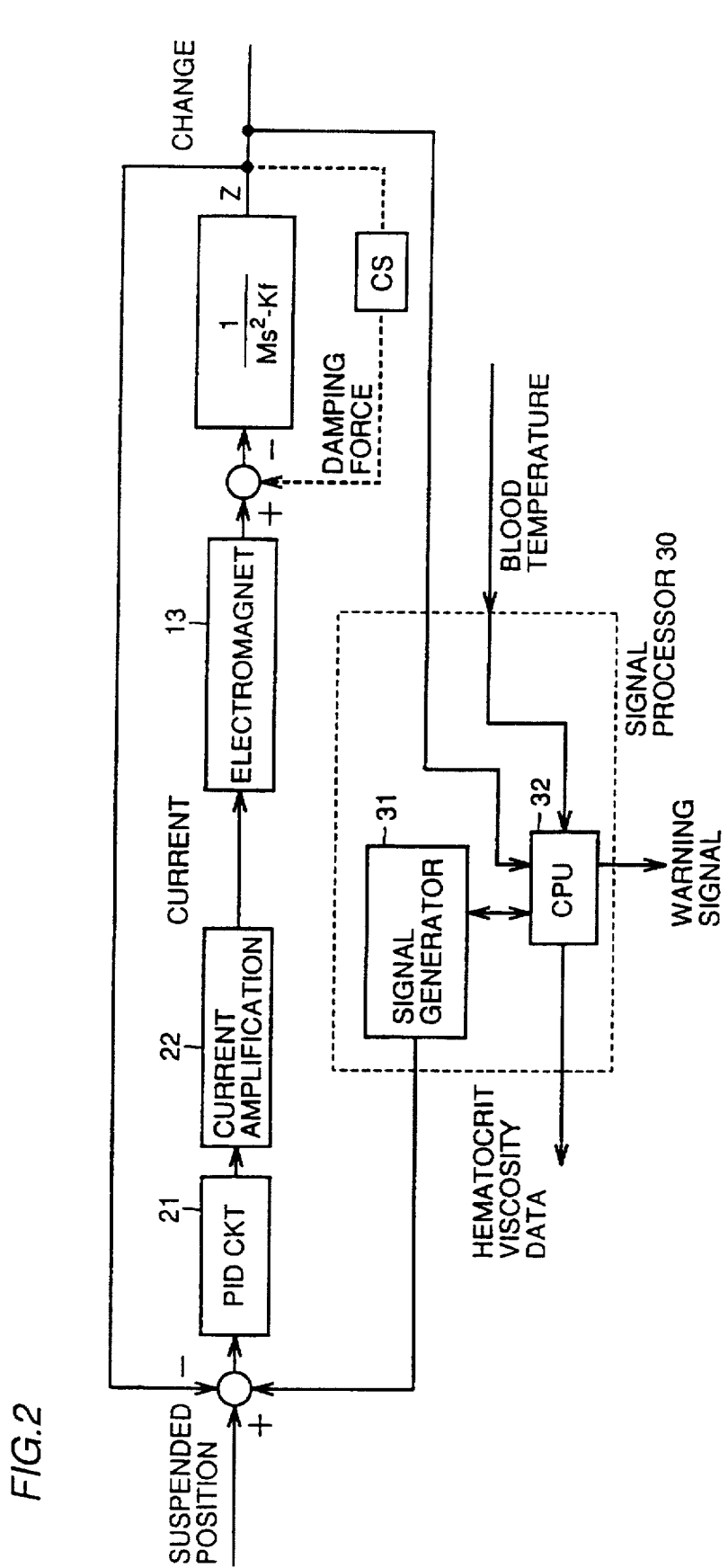
FIG. 2 is a block diagram showing the embodiment of the present invention.

FIG. 2 is a block diagram showing the embodiment of the invention. The active magnetic bearing according to the embodiment is of a 3-axes type as described in conjunction with FIG. 1, and therefore three control loops denoted in solid line in FIG. 2 are provided, and Z, $\theta_x$ and $\theta_y$ are controlled by these control loops. FIG. 2 shows only the Z-axis control loop.

A PID circuit 21 is a compensation circuit, the output of which is current-amplified by an amplifier 22 to control electromagnet 13. $1/(Ms^2-Kf)$ in FIG. 2 is a transfer function representing an object to be controlled by the magnetic bearing. Cs represents viscosity damping when rotor 6 is suspended in liquid.

Furthermore, there is provided a signal processor 30 characteristic to the invention. Signal processor 30 is formed of a signal generator 31 and a CPU 32. Signal generator 31 generates a step signal of constant voltage, and the signal is added to a rotor suspended position signal. The electrical signal changes the position of suspended rotor 6. The speed of the change is affected by the damping coefficient C of the liquid. CPU 32 produces the viscosity of the liquid by an operation based on the relation between previously measured rotor response time and viscosity. Since the viscosity and the damping coefficient are equivalent, the viscosity can readily be operated based on the response time. CPU 32 can additionally produce useful medical information such as hematocrit based on the temperature of blood and the calculated viscosity. Table 1 shows results of measurements of the viscosity, hematocrit and temperature of human blood using a rotary conical type viscosimeter, and shows that the hematocrit can be estimated based on the temperature and viscosity of blood.

TABLE 1

| Blood Temp. | Hematocrit % | | | |
|---|---|---|---|---|
| °C. | 20 | 30 | 40 | 50 |
| 20 | 4.0 | 5.2 | 7.8 | 9.1 |
| 30 | 2.9 | 3.8 | 4.6 | 5.8 |
| 37 | 2.0 | 3.1 | 3.9 | 4.8 |

Cp: Unit of viscosity

A usual flow meter generates an error by a change in viscosity, the viscosity obtained here can be utilized for calibrating a flow meter, and therefore flow rates can be measured highly precisely. For higher blood viscosity, thrombi are prone to form, and the blood viscosity sometimes drops by bleeding. Therefore, CPU 32 outputs a warning signal if a result of measuring viscosity indicates a value excessively higher or lower than a tolerance value for viscosity, so that a doctor or a patient himself/herself can quickly cope with the situation.

Figure 3A:
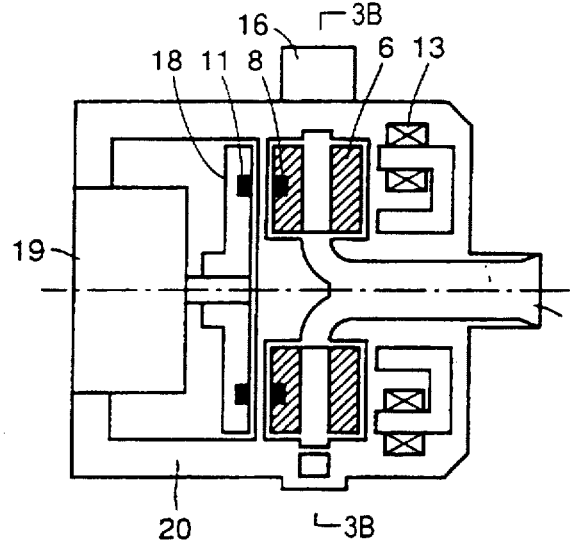
FIGS. 3A and 3B include views showing a blood pump to which the present invention is applied.
Figure 3B:
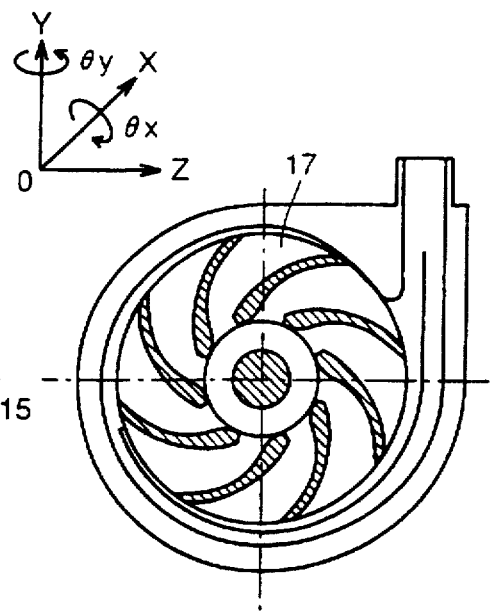

FIGS. 3A and 3B show a blood pump to which the present invention is applied, in which FIG. 3A is a side view in section, and FIG. 3B is a cross sectional view taken along 3B—3B in FIG. 3A. The example shown in FIGS. 3A and 3B is provided with an impeller 17 in place of rotor 6 shown in FIGS. 1A to 1C. A permanent magnet 8 is provided on one side of impeller 17, and at a rotor 18 a permanent magnet 11 is provided facing opposite to permanent magnet 8. Rotor 18 is driven to rotate by a DC motor 19, and the magnetic coupling of permanent magnets 8 and 11 rotates impeller 17. Signal generator 31 described in conjunction with FIG. 2 provides a step signal to an electromagnet 13 provided on the other side of impeller 17, impeller 17 moves accordingly, and the response upon moving is detected by the position sensor.

Figure 4:
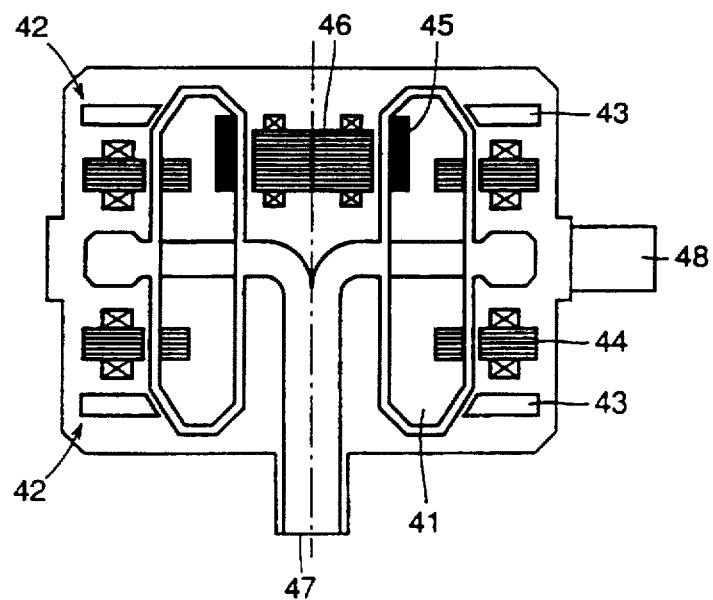
FIG. 4 is a view showing another example of blood pump.

FIG. 4 shows another example of blood pump. In FIG. 4, an impeller 41 is actively supported by two radial magnetic bearings 42. Radial magnetic bearing is formed of a position sensor 43, an electromagnet 44, and a controller which is not shown. A permanent magnet 45 attached to impeller 41 and a stator 46 form a DC brushless motor and impeller 41 rotates accordingly. Fluid is input from an inlet 47 and output from an outlet 48 under increased pressure by the rotation of impeller 41.

Also in this embodiment, electromagnet 44 is provided with a step signal from signal generator 31 shown in FIG. 2, and the response of the rotor is detected by the position sensor.

Figure 5A:
FIGS. 5A and 5B include charts showing the response characteristic of an impeller when the position of suspending the impeller is changed stepwise.
Figure 5B:
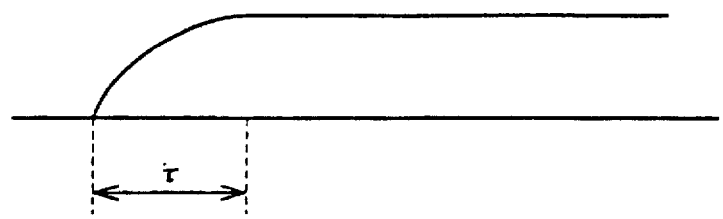
Figure 6:
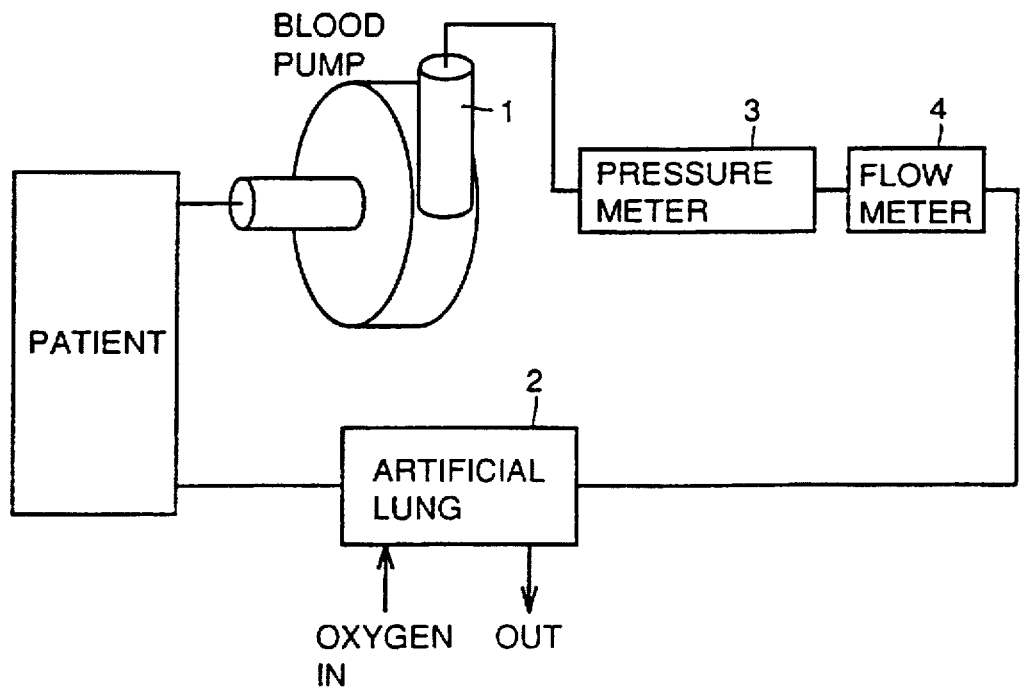
FIG. 6 shows a conventional artificial heart-lung machine.

FIGS. 5A and 5B show the response of the impeller when the position of the suspended impeller is changed stepwise. As the liquid viscosity increases, time until the impeller is stabilized at a fixed position is prolonged. As shown in FIG. 5A, the viscosity can be produced by measuring τ shown in FIG. 5B as the suspended position signal is changed stepwise.

As described above, according to the present invention, the rotor is suspended in fluid, the suspended position of the rotor is changed stepwise, the viscosity of the fluid is produced based on the response time of the rotor during the change, and therefore the blood viscosity can be measured in real time. In addition, by combining the temperature and the viscosity, blood information can be obtained without actually collecting blood. Furthermore, issuing a warning about abnormal blood viscosity makes possible quick treatment to a patient with an artificial heart.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. Apparatus for measuring a liquid viscosity, comprising:
   a rotor;
   a magnetic bearing for suspending said rotor in a liquid; and means for producing a stepwise change in a position of said suspended rotor and for determining a response time for said rotor to respond to the stepwise change and thereby determining a viscosity of the liquid.

2. The apparatus according to claim 1, further comprising:
   rotation driving means for rotating said rotor in a non-contact manner and making said rotor function as a pump.

3. The apparatus according to claim 2, further comprising:
   a temperature sensor for detecting a temperature of said liquid,
   wherein said means for producing said stepwise change includes operation means for operating a hematocrit based on a calculation result of a temperature detected by said temperature sensor and said determined viscosity of the liquid.

4. The apparatus according to claim 3, wherein:
   said operation means outputs a warning signal if said liquid viscosity reaches a predetermined value.

5. A device for measuring a viscosity of a liquid, comprising:
   a casing member containing the liquid;
   an impeller rotated within said casing member;
   an active magnetic bearing provided on one side of said casing member for pivotally supporting one side of said impeller;
   rotation means provided on another side of said casing member for rotating said impeller while pivotally supporting the said impeller; and
   viscosity measuring means for changing a suspension position of said impeller in a stepwise manner and for measuring the viscosity of said liquid based on a response time of said impeller to the stepwise change in position.

6. The apparatus according to claim 5, wherein:
   said impeller has a first permanent magnet provided at one surface and a magnetic member provided on another surface;
   said active magnetic bearing includes an electromagnet positioned facing the magnetic member of said impeller through said casing member; and
   said rotation means includes an electric motor, a second permanent magnet provided opposite to the first permanent magnet of said impeller through said casing member, said first and second permanent magnets attracting each other, and a rotor driven to rotate by said electric motor.

* * * * *